United States Patent [19]
deVial et al.

[11] 4,057,721
[45] Nov. 8, 1977

[54] OIL POLLUTION MONITORING AND MONITORING UNIT

[75] Inventors: Raymond Michael deVial, Beckenham; Philip Maurice Taylor, Croydon, both of England

[73] Assignee: Bailey Meter & Controls Limited, England

[21] Appl. No.: 684,838

[22] Filed: May 10, 1976

[30] Foreign Application Priority Data
May 8, 1975 United Kingdom ............... 19359/75

[51] Int. Cl.$^2$ ............................................. G01T 1/169
[52] U.S. Cl. .................................... 250/301; 250/343
[58] Field of Search ................ 250/301, 458, 459, 343

[56] References Cited
U.S. PATENT DOCUMENTS

| | | | |
|---|---|---|---|
| 2,918,579 | 12/1959 | Slobod et al. | 250/301 X |
| 3,462,596 | 8/1969 | Saunders | 250/301 |
| 3,649,833 | 3/1972 | Leaf | 250/458 X |
| 3,917,945 | 11/1975 | Sema et al. | 250/301 |

Primary Examiner—Archie R. Borchelt
Attorney, Agent, or Firm—Kemon & Estabrook

[57] ABSTRACT

An oil-contaminated water stream is monitored by continuously exciting and measuring fluorescence in the stream at a monitoring point and producing a continuous monitoring indication accordingly, recurrently withdrawing from the stream samples of the contaminated water, determining the oil content of each sample by an infra-red absorption procedure, comparing each oil determination with the monitoring indication pertaining to the appropriate part of the stream and correcting or recalibrating the monitoring indication accordingly.

6 Claims, 2 Drawing Figures

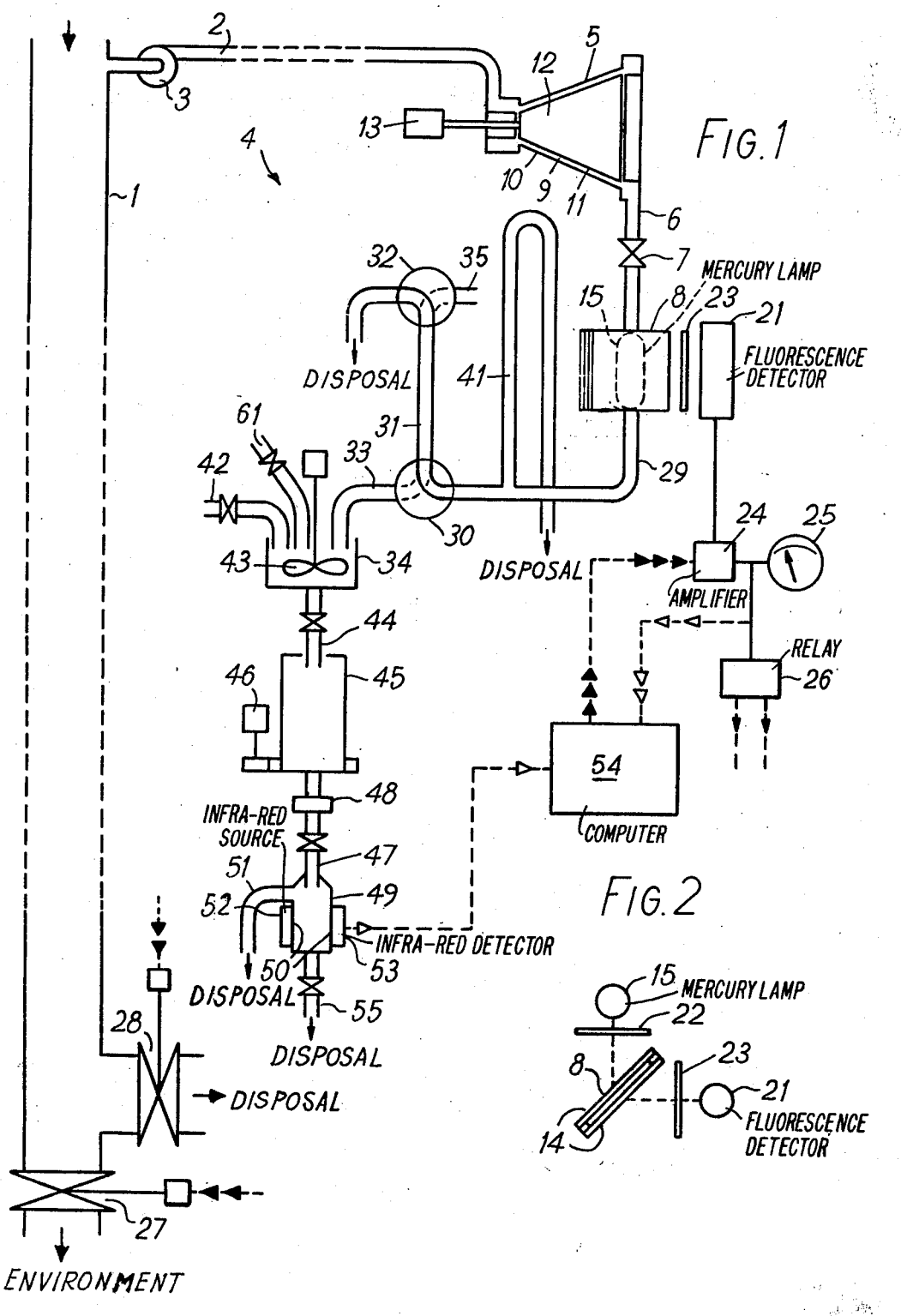

OIL POLLUTION MONITORING AND MONITORING UNIT

BACKGROUND OF THE INVENTION

This invention relates to the monitoring of a fluid stream in respect of its contamination content.

An important need to monitor contaminated fluid streams or streams capable of becoming contaminated arises where a fluid is to be discharged to waste so long as it does not unacceptably pollute the environment. One of the less tolerable pollutants is oil, which may be a variable constituent of industrial effluents intended to be discharged into rivers, a variable contaminant of water pumped from ships' bilges and a varying contaminant of sea-water ballast to be discharged from cargo tanks of oil tankers.

It is possible to take a discrete sample of a water stream contaminated with oil and to determine the degree of contamination of the water by the oil. One effective method of operating on a sample to this end involves agitating with the sample a liquid solvent of the oil, allowing the resultant oil/solvent solution to settle from the water and measuring the power of the oil/solvent solution to absorb infra-red radiation. However, so far as we know, this procedure is not capable of being converted otherwise than in a complex way from a process using discrete samples to a continuous process and is in any event not capable of being converted to a continuous process giving instantaneous or nearly instantaneous dertreminations so as to make possible useful continuous monitoring of fast-moving partially contaminated fluid streams. Monitoring units have therefore been devised exploiting the property of oil of being excitable into fluorescence, which have allowed of continuous practically instantaneous monitoring of oil-contaminated water streams and have operated very effectively, more particularly for supervising the discharge of sea-water ballast from oil tankers with monitoring of its degree of oil content.

SUMMARY OF THE INVENTION

The present invention provides a method of continuously monitoring a water stream in respect of its contamination content of oil, including continuously exciting fluorescent radiation in the stream as it passes a monitoring point and producing a continuous monitoring indication dependent upon a measure of the amount of fluorescent radiation so excited, recurrently withdrawing from the stream samples of the contaminated water and making by an infra-red absorption producedure respective determinations of the degrees of contamination of said samples by oil and recurrently re-calibrating or correcting the monitoring indication in dependent upon respective comparisons between the determinations and those monitoring indications that pertained to the respective moving parts of the stream from which the respective discrete samples were withdrawn.

This method exploits the fluorescible property of oil to allow of continuous practically instantaneous monitoring. The monitoring indications are automatically recurrently re-calibrated or corrected by reference to determinations made within the range of oil pollutions of the water which are actually experienced, with the avoidance or suppression therefore of indication errors that might be present if the monitoring unit were calibrated only by the use of an artificial flow to which has been given an arbitrary degree of oil contamination.

The method also effects certain compensations if some parameters or assumed constants of the monitoring procedure change, for example, if there occurs a change in the degree of dispersion of the contamination oil in the water effected by an emulsifier arranged to operate on the stream before it is passed to the fluorescence-exciting and fluorescence-detecting point. The method, moreover, may allow of a wider use of monitoring exploiting the fluorescible properties of oil, for the monitoring indications are, if necessary, re-calibrated or corrected if the contamination content of the stream comes to change in the type of oil, which for the same degree of contamination may yield a higher or a lower fluorescence.

The invention also provides a unit for monitoring a water stream in respect of its contamination content of oil, adapted for operating according to the method indicated, which includes means for exciting fluorescence in the stream, means for producing a monitoring indication dependent upon the content of fluorescence excited, oil-determining means capable of determining by an infra-red absorption procedure the oil content of a sample of the stream and a computer which is arranged for supervising the operation of the oil-determining means which includes a timer for causing the recurrent operation of the oil-determining means and which is arranged to compare after each such recurrent operation the oil determination and the monitoring indication that pertained to the part of the stream from which the appropriate sample was withdrawn and to correct or re-calibrate the monitoring indication accordingly.

BRIEF DESCRIPTION OF THE DRAWINGS

The invention will now be described by way of example with reference to the accompanying drawings, in which FIG. 1 shows schematically a monitoring unit arranged for monitoring a contaminated fluid stream and FIG. 2 is a schematic plan of some of the elements of the monitoring unit represented in elevation in FIG. 1.

DETAILED DESCRIPTION OF THE DRAWINGS

With reference to FIG. 1 of the drawings, for the supervising of a flow to the environment of oil-contaminated water pumped along a conduit 1, for example, oil-contaminated sea-water intended for discharge to the sea from an oil tanker, a continuous specimen or sampling stream is withdrawn from the flow through a pipe 2 containing a pump 3 and delivered along the pipe 2 to a monitoring unit 4. The monitoring unit 4 may well be remote from the conduit 1 and if so the pump 3 is arranged to give a high flow speed in order to reduce delay in the monitoring due to the necessary length of the pipe 2.

In the monitoring unit the pipe 2 leads to the inlet of a sample conditioning unit or emulsifier 5, from the outlet of which a pipe 6 with a constant flow valve 7 leads to an inspection chamber 8 allowing of continuous inspection of the sampling stream.

The sample conditioning unit 5 is a high shear rotating mechanical mixer adapted to disperse the contaminating oil content of the sampling stream throughout the said stream. In the suitable construction shown, the sampling stream flows in the sample conditioning unit from the narrow end to the wider end of an annular space 9 defined outwardly by a stationary frusto-conical surface 10 and defined inwardly by a frusto-conical surface 11 of a rotary member 12 driven by a motor 13. The frusto-conical surface 10 and/or the frusto-conical surface 11 may be provided with grooves, which may be helical-spiral, and/or with vanes, which may be helical-spiral, projecting into the annular space 9, with the aid of which to increase the eddying and shearing effects in the sampling stream passing through the conditioning unit and thereby to improve the dispersal of the oil content throughout the stream. The maximum oil particle size in the stream leaving the sample conditioning unit should be 5 microns.

With reference also to FIG. 2, the inspection chamber 8 is shown as a flat cell comprising a pair of glass or quartz windows 14 one parallel to the other. A mercury vapour lamp 15 is arranged to direct a beam of ultra-violet radiation through one of the windows 14 into the sampling stream passing through the cell between the windows and a photo-multiplier 21 is arranged to receive and to respond to fluorescent radiation excited in the sampling stream in the cell and emitted through the other of the windows 14. A filter 22 is interposed in the beam from the lamp 15 and a filter 23 is interposed in the fluorescent radiation path to the photo-multiplier 21; suitably the filter 22 passes a narrow band of wavelengths centered on 365 nanometers while the filter 23 passes wavelengths above 400 nanometers. The centre line of the beam of ultraviolet radiation directed by the lamp 15 onto the cell and the centre line of the field of view of the cell of the photo-multiplier 21 are at right angles one to the other and the mid-plane of the cell 8 bisects the right angle between the two centre lines. Optical focusing means (not shown) may be provided to increase the irradiation of the cell by the lamp 15 and the irradiation of the photo-multiplier 21 by fluorescent radiation from the cell.

Preferably, wipers (not shown) within the cell but operated from outside the cell are provided for periodically making a reciprocating movement from one side of the cell to the other and back to remove oil that may be clinging to the inner faces of the two windows 14.

The response of the photo-multiplier 21 is passed through a variable-gain amplifier 24 to means 25 for indicating the degree of contamination of water by oil, as shown said means positioning a display needle in front of a graduated scale; alternatively or in addition a recording pen may be positioned on a graduated moving chart.

In the supervising of the flow along the conduit 1 by monitoring of the sampling stream, the output of the amplifier 24 is also led to a relay 26 arranged to cut off the discharge through the conduit 1 to the environment if the amplifier output signals an oil content of the sampling stream that is above a predetermined amount. The environment may be so protected by closing a discharge valve 27 at the end of the conduit 1 and simultaneously opening a diversion valve 28 from the conduit 1 to an alternative disposal as, for example, by leading the conduit flow back to the oil tanker tank being flushed; the pairs of black arrowheads designate such a control by the relay 26 of respective operating means of the valves 27 and 28. The relay 26, instead of or as well as controlling such valves, may operate to control whatever pump is responsible for the flow along the conduit 1.

A pipe 29 leads the stream after its passage through the inspection chamber 8 to a two-way valve 30, which in the usual of its two positions, shown in full lines, connects the pipe 29 to the lower end of a vertical pipe length 31 leading at its upper end to a second two-way valve 32. The second two-way valve 32 in the usual of its two positions, shown in full lines, connects the pipe length 31 to disposal.

The third connection 33 of the two-way valve 30 leads to a mixing vessel 34 and the third connection 35 of the two-way valve 32 leads to atmosphere. If simultaneously the valves 30 and 32 are both turned 90° anti-clockwise to their alternative positions, shown in dashed lines, the liquid contents of the vertical pipe 31, together with the liquid contents of the channels in the two valves, flow into the mixing vessel 34. This operation is performed recurrently, the valves 30 and 32 being on each occasion returned to their original, normal positions immediately after the elapse of a period sufficient to allow the said quantity of liquid to flow into the mixing vessel. Adjacent the entry to the two-way valve 30 the pipe 29 is connected to one end of an inverted U-tube 41 through which the stream can be passed to disposal during the times that the two-way valve 30 is closed to it.

Whenever by operation of the two-way valves 30 and 32 a fixed-volume sample of the stream is allowed to run into the mixing vessel 34, a fixed quantity of tetrachlor-ethylene or other suitable oil-dissolving solvent is also supplied to the mixing vessel through a valved pipe 42 and the contents of the mixing vessel are then stirred together. The stirring means, shown conventionally as a simple rotary paddle 43, may in fact comprise a system of rotary vanes driven through apertures in a labyrinthine array of stationary vanes.

After a predetermined stirring time sufficient for the absorption of substantially all the oil in the solvent, the contents of the mixing vessel 34 are allowed to run through a valved pipe 44 into a whirl chamber 45 of vertical rotary axis, which is then rotated at speed by a motor 46 until the water and the oil/solvent solution separate from one another. The motor 46 is then slowed and stopped, whereupon the water is found in a layer above the oil/solvent solution. A valved pipe having a rotary connection therein leads from the centre of the whirl chamber base vertically downwardly to a windowed cell 49 preferably not large enough to contain the whole of the oil/solvent solution; when the whirl chamber is drained through the pipe 47 after a separation, oil/solvent solution occupies the cell space between the windows 50 thereof and excess liquid flows away through an overflow 51.

Through one of the cell windows 50 infra-red radiation is directed into the oil/solvent solution towards the other window from a source 52 outside the cell of infra-red radiation comprising an infra-red lamp and a filter adapted to pass a narrow band of wave-lengths centred on 3417 nanometers. Outside the cell on the other side thereof to receive from the source 52 infra-red radiation which has not been absorbed by the oil/solvent solution in the cell are infra-red detecting means 53. The greater the amount of oil in the solution, the greater the absorption of infra-red radiation by the solution and the smaller the amount of infra-red radiation detected by the means 53. The relation between the absorption of infra-red radiation by the solution and the amount of oil in the solution is, as is known, a non-linear one. The output of the infra-red detector 53 when it measures the infra-red absorption by the oil/solvent solution and also the output of the infra-red detector when for standardizing purposes it is arranged to measure the infra-red absorption when clean solvent is for the purpose placed in the cell are both led to a computer 54 which is arranged to convert the two outputs into a determination of the oil content of the fixed-volume sample withdrawn from the sampling stream.

A valved pipe 55 leads from the base of the cell 51, through which cleaning or flushing fluid, supplied through a valved pipe 61 leading to the mixing vessel 34, can be discharged after passing through the mixing vessel 34, the valved pipe 44, the whirl chamber 45, the valved pipe 47 and the cell 49.

The sequence of operations necessary to carry out an oil determination by the infra-red absorption procedure, which should normally be less than 10 minutes and which we believe is feasible to be performed within 5 minutes, is under the control of the computer 54, which also includes a timer which will ensure repetition of the necessary sequence recurrently. In each sequence, the first operation may be a standardizing one with the cell 49 filled with solvent, thereafter discharged. The two-way valves 30 and 32 will be temporarily operated to ensure a flow into the mixing vessel 34 from the sampling stream of a discrete sample of the oil contaminated water; the valved pipe 42 will be temporarily opened to admit into the mixing vessel a fixed quantity of solvent; the stirring means 43 will be operated for a suitable length of time; the valved pipe 44 will be opened to admit the formed mixture into the whirl chamber 45, which is then spun for a suitable period, slowed and stopped; the valved pipe 47 is opened to admit the contents of the whirl chamber 45 in separated form into the cell 49, in which sufficient oil/solvent solution remains but from which the water and excess oil/solvent solution overflows; after the infra-red absorption of the solution in the cell 49 has been measured, the valved pipes 61 and 55 are opened to effect cleaning of the apparatus, after which the valved pipes 61, 44, 47 and 55 are reclosed, and the apparatus is ready for another oil determination by infra-red absorption procedure.

As mentioned, and as indicated by the signal line between the two single white arrowheads, the response of the infra-red detector 53 is led to the computer 54 and the computer is arranged to convert, during the period when the cell 49 contains the oil/solvent solution, the response of the said detector, taking a previous standardizing into account, into a percentage measue of the amount of oil in the discrete sample of contaminated water withdrawn from the sampling stream. As indicated by the signal line between the two double white arrowheads the output of the amplifier 24, that is to say, in effect the indicated degree of contamination of water by oil, is also led to the computer, which is arranged to effect a comparison between the oil determination made by the infra-red absorption procedure and the indicated degree of contamination of water by oil. In order to compensate for the time taken in determining the oil content by infra-red absorption procedure, the computer is arranged to retain, for example in an integrated-circuit memory, until the infra-red response of an oil determination by infra-red absorption procedure is available, the response of the photo-multiplier 21 pertaining to the identical part of the sampling stream that, shortly after leaving the inspection chamber 8, supplied the fixed-volume sample withdrawn into the mixing vessel. The computer is therefore able to make a comparison between the oil percentage in the water as determined by infra-red absorption procedure and the indicated oil percentage in respect of the same part of the sampling stream.

As indicated by the control line between the two treble black arrowheads a computer output is led to the amplifier 24 in the signal line from the photo-multiplier 21 to the indicating means 25 and the computer is arranged to re-adjust the gain of the amplifier 24 in accordance with the said comparison, thereby, so far as necessary, to re-calibrate or correct the indications of the indicating means 25. Thus, for example, if the comparison shows that, in respect of a part of the sampling stream, the oil percentage determined by infra-red absorption procedure is 5% greater than the oil percentage displayed by the indicating means in respect of the same part of the sampling stream, then the gain of the amplifier 24 is re-adjusted by the computer 54 to cause the indicating means 25 to indicate from that moment until the next recurrent oil determination an oil percentage 5% higher than it would have done in the absence of the amplifier re-adjustment.

As mentioned, the computer includes a timer which will ensure repetition recurrently of the sequence of operations necessary to carry out an oil determination by the infra-red absorption procedure. It depends upon the source of the oil-contaminated flow along the conduit 1 whether the timer should be set to ensure more frequent oil determinations by the infra-red procedure during the time of the flow, or whether it suffices for it to be set for less frequent oil determinations. It may well be a wise precaution to arrange that the computer ensure very frequent oil determinations by the infra-red procedure during the initial period of a flow, both in order to check as early as possible whether expectations as to the amounts of oil contaminant in the particular flow are realized and in order to effect as early as possible the automatic calibration of the monitoring indications; the computer may be arranged, at the end of a pre-determined sequence of several oil determinations by the infra-red procedure at frequent intervals to revert to effecting recurrently oil determinations at normal, less frequent intervals. It may be in some cases that the oil contamination is likely to vary in some unforeseeable way towards the end of a flow and in this case also it would be advantageous to set the computer for very frequent oil determinations by the infra-red procedure.

It may be arranged that if the monitoring indication changes by more than a perdetermined amount, then the computer, which receives the monitoring indication signal, immediately effects the making of an oil determination and the re-calibrating of the monitoring indication accordingly, whether or not the timer would have dictated such an action in the near future, this interjected oil-determination/re-calibrating action being then treated as the first of a replacement sequence of recurrent oil-determination/re-calibrating actions at the normal intervals.

Before a series of recurrent oil determinations by the infra-red procedure it will be advantageous to arrange that the amplifier 24 is at least approximately appropriately adjusted in relation to the expected oil type and quantity. If there has been a previous such series in connection with a previous similar flow in the conduit, one might well arrange for the computer to memorize the previous adjustment of the amplifier and to apply it automatically to the amplifier 24 even before the first oil determination of the new series.

The described method and apparatus achieves continuous monitoring with a high accuracy owing to the recurrent recalibrations which are effected whatever the ranges of oil content that are encountered and which automatically compensate for any special characteristics of the apparatus there may be and for any changes in parameters or assumed constants of the monitoring by the fluorescence procedure; for example, monitoring by a fluorescence procedure is known to be sensitive to the quality of the dispersion of oil in the water but if the sample conditioning unit 5 should change its efficiency somewhat the next re-calibration would correct the difference that would otherwise be made in the monitoring indications. Changes in the type of oil which will increase or reduce the fluorescence are also automatically compensated for.

In the monitoring unit described the fixed-volume samples for oil determination are withdrawn from the stream which leaves the inspection chamber 8. The fixed-volume samples for oil determination in a modified unit, however, is withdrawn from the stream before it enters the sample-conditioning unit 5, the monitoring indication placed on store in the computer 54, for subsequent comparison with the oil determination made in respect of the sample, then being chosen to pertain to the same part of the stream from which the sample was withdrawn but of course cannot pertain to the sample itself.

We claim:

1. A method of continuously monitoring a water stream in respect of its contamination content of oil, including continuously exciting fluorescent radiation in the stream as it passes a monitoring point and producing a continuous monitoring indication dependent upon a measure of the amount of fluorescent radiation so excited, recurrently withdrawing from the stream discrete samples of the contaminated water and making by an infra-red absorption procedure respective determinations of the degree of contamination of said samples by oil, each infra-red absorption procedure comprising adding to the sample a solvent for the oil, separating out from the water of the sample a solution of the oil in the solvent and measuring the infra-red absorption capability of the percentage of oil in the solution, and recurrently recalibrating or correcting the monitoring indicating in dependence upon respective comparisons between the determinations and those monitoring indications that pertained to the respective moving parts of the stream from which the respective discrete samples were withdrawn.

2. A method as claimed in claim 1, wherein the withdrawing of the samples from the stream is effected after the stream has passed the monitoring point.

3. A method as claimed in claim 2, wherein each comparison is made between an oil determination and a monitoring indication pertaining to the identical part of the stream that yielded the discrete sample of which the oil content was determined.

4. A method as claimed in claim 1, wherein each sample is withdrawn by temporarily isolating a length of pipe carrying the stream and removing the contents of said length of pipe by gravity.

5. A method as claimed in claim 1, wherein the oil determination of each sample includes stirring the sample with an oil solvent, separating out from the water of the sample by centrifugal force the resulting oil/solvent solution and measuring the absorption by the solution of infra-red radiation directed into the solution through a cell window.

6. A unit for monitoring a water stream in respect of its contamination content of oil, which includes means for exciting fluorescence in the stream, means for producing a monitoring indication dependent upon the amount of fluorescence excited, means for withdrawing from the stream a discrete sample of the contaminated water, oil-determining means capable of determining by an infra-red absorption procedure the oil content of the said sample, said oil-determining means comprising means for adding to the sample a solvent for the oil, means for effecting a separating out from the water of the sample solution of the oil in the solvent and means for measuring the infra-red absorption capability of the percentage of oil in the solution, and a computer which is arranged for supervising the operation of the oil-determining means and which includes a timer for causing the recurrent operation of the oil-determining means and which is arranged to compare after each such recurrent operation the oil determination and the monitoring indication that pertained to the part of the stream from which the appropriate sample was withdrawn and to correct or re-calibrate the monitoring indication accordingly.

* * * * *